(12) United States Patent
Sigurjonsson et al.

(10) Patent No.: US 8,568,795 B2
(45) Date of Patent: Oct. 29, 2013

(54) STABILIZED FORMULATION COMPRISING OMEGA-3 FATTY ACIDS FOR SKIN CARE AND/OR WOUND CARE

(75) Inventors: Gudmundur Fertram Sigurjonsson, Reykjavik (IS); Biljana Ilievska, Isafjordur (IS); Baldur Tumi Baldursson, Reykjavik (IS)

(73) Assignee: Kerecis EHF, Reykjavik (IS)

( * ) Notice: Subject to any disclaimer, the term of this patent is extended or adjusted under 35 U.S.C. 154(b) by 0 days.

(21) Appl. No.: 13/114,106

(22) Filed: May 24, 2011

(65) Prior Publication Data

US 2011/0293755 A1 Dec. 1, 2011

Related U.S. Application Data

(60) Provisional application No. 61/348,357, filed on May 26, 2010.

(51) Int. Cl.
| A61K 36/00 | (2006.01) |
| A61K 36/67 | (2006.01) |
| A61K 36/53 | (2006.01) |
| A61K 36/537 | (2006.01) |
| A61K 36/8962 | (2006.01) |
| A61K 36/906 | (2006.01) |

(52) U.S. Cl.
USPC ........... 424/725; 424/734; 424/745; 424/746; 424/754; 424/756

(58) Field of Classification Search
None
See application file for complete search history.

(56) References Cited

U.S. PATENT DOCUMENTS

| 2006/0198800 A1* | 9/2006 | Dilallo et al. ................ 424/59 |
| 2006/0251750 A1* | 11/2006 | Tabor .......................... 424/757 |
| 2007/0243307 A1 | 10/2007 | Abril et al. |
| 2008/0050475 A1* | 2/2008 | Garter et al. .................... 426/96 |
| 2010/0021573 A1* | 1/2010 | Gonzalez et al. ............. 424/766 |
| 2010/0272669 A1* | 10/2010 | Malessa et al. ............. 424/78.03 |
| 2011/0008457 A1 | 1/2011 | Newman et al. |
| 2011/0091580 A1* | 4/2011 | He et al. ........................ 424/725 |

FOREIGN PATENT DOCUMENTS

| EP | 0699437 A1 | 3/1996 |
| EP | 1637130 A1 | 3/2006 |
| GB | 2458466 A | 9/2009 |
| GR | 1004395 B1 | 11/2003 |
| JP | 2003113017 A * | 4/2003 |
| WO | 0049889 A1 | 8/2000 |
| WO | 2011057183 A1 | 5/2011 |

OTHER PUBLICATIONS

Engstrom, Karin, et al., Effect of fish oils containing different amounts of EPA, DHA, and antioxidants on plasma and brain fatty acids and brain nitric oxide synthase activity in rats, UPSALA Journal of Medical Sciences, vol. 114, No. 4, Dec. 1, 2009, pp. 206-213, XP55005475.
International Search Report dated Aug. 31, 2000 for PCT/IB2011/001113.
Written Opinion of ISA in PCT/IB2011/001113, and ISR in PCT/IB2011/001113, Aug. 31, 2011.

* cited by examiner

Primary Examiner — Qiuwen Mi
(74) Attorney, Agent, or Firm — Workman Nydegger

(57) ABSTRACT

A stabilized formulation for skin care, wound care and/or other tissue healing applications and methods for making the same is described. The stabilized formulation stabilizes omega-3 polyunsaturated fatty acids and is constituted of the omega-3 polyunsaturated fatty acids in combination with tocopherol (Vitamin E), ascorbic acid (Vitamin C), herb extract, and a fat-soluble antioxidant. Methods for making and using the stabilized formulation are also described.

18 Claims, 2 Drawing Sheets

FIGURE 2

FATTY ACID COMPOSITION

| Peak # | Component Name | Time [min] | Area [%] | Total omega-3 A% | Satur. fatty acid A% | monounsatur. fatty acid A% | Polyunsatur. fatty acid A% |
|---|---|---|---|---|---|---|---|
| 1 | C14:0 | 6,730 | 7,35 | 0,00 | 7,35 | | 0,00 |
| 2 | | 7,692 | 0,54 | | | | |
| 3 | C16:0 | 8,906 | 17,04 | 0,00 | 17,04 | | 0,00 |
| 4 | C16:1 | 9,258 | 8,85 | 0,00 | 0,00 | | 8,85 |
| 5 | | 9,639 | 0,43 | | | | |
| 6 | | 10,124 | 1,12 | | | | |
| 7 | | 10,399 | 0,41 | | | | |
| 8 | | 10,663 | 1,52 | | | | |
| 9 | C16:4 n-1 | 11,661 | 2,62 | 0,00 | 0,00 | | 2,62 |
| 10 | C18:0 | 12,222 | 3,33 | 0,00 | 3,33 | | 0,00 |
| 11 | C18:1-n 9 | 12,591 | 9,50 | 0,00 | 0,00 | 9,50 | 0,00 |
| 12 | C18:1 n-7 | 12,732 | 3,12 | 0,00 | 0,00 | 3,12 | 0,00 |
| 13 | C18:2 n-6 | 13,521 | 1,21 | 0,00 | 0,00 | | 1,21 |
| 14 | | 13,974 | 0,44 | | | | |
| 15 | C18:3 n-3 | 14,944 | 0,79 | 0,79 | 0,00 | 0,00 | 0,79 |
| 16 | C18:4 n-3 | 15,656 | 3,16 | 3,16 | 0,00 | 0,00 | 3,16 |
| 17 | C20:1 | 17,133 | 1,11 | 0,00 | 0,00 | 1,11 | 0,00 |
| 18 | C20:4 n-6 | 19,544 | 0,94 | 0,00 | 0,00 | 0,00 | 0,94 |
| 19 | C20:4 n-3 | 20,708 | 0,72 | 0,72 | 0,00 | 0,00 | 0,72 |
| 20 | C20:5 n-3 | 21,312 | 19,60 | 19,60 | 0,00 | 0,00 | 19,60 |
| 21 | C22:1 | 22,275 | 0,69 | 0,00 | 0,00 | 0,69 | 0,00 |
| 22 | C21:5 n-3 | 24,267 | 0,78 | 0,78 | 0,00 | 0,00 | 0,78 |
| | C22:5 n-6 | 25,885 | 0,00 | | | | |
| 23 | C22:5 n-3 | 26,982 | 2,15 | 2,15 | 0,00 | 0,00 | 2,15 |
| 24 | C22:6 n-3 | 27,801 | 12,59 | 12,59 | 0,00 | 0,00 | 12,59 |
| | C24:1 | 28,024 | 0,00 | | | | |
| | | | 100,00 | 39,79 | 27,73 | 23,25 | 44,56 |

STABILIZED FORMULATION COMPRISING OMEGA-3 FATTY ACIDS FOR SKIN CARE AND/OR WOUND CARE

RELATED APPLICATIONS

This application claims benefit of U.S. Provisional Application No. 61/348,357, filed on May 26, 2010, the entire contents of which are incorporated herein by reference.

FIELD

This invention relates to a formulation for stabilizing omega-3 polyunsaturated fatty acids. The formulation comprises the omega-3 polyunsaturated fatty acids in combination with tocopherol (Vitamin E), ascorbic acid (Vitamin C), herb extract, and a fat-soluble antioxidant. This stabilized formulation retards omega-3 polyunsaturated fatty acid oxidation and degradation so that the fatty acids can be used in cosmetic and pharmaceutical creams for treatment of various skin conditions and wounds.

BACKGROUND

The outermost layer of the skin consists of 15 to 20 cell layers of living cells that die and dry out to build the corneal layer of the skin. Between the dried cells is the intercellular substance, which is rich in epidermal lipids to keep the structure intact and watertight. The corneal layers of the skin are prone to lose the intercellular lipids. The result is that the corneal layer looses volume and no longer protects the living cells inside. This may lead to inflammation, callosities and fissures. Fatty acids can be applied to the skin to increase the amount of intercellular lipids in the skin.

Omega-3 fatty acids (also known as ω-3 fatty acids or n-3 fatty acids) are a family of unsaturated fatty acids that have a final carbon-carbon double bond in the n-3 position (i.e. the third bond from the methyl end of the fatty acid). Oils derived from marine sources contain high proportions of the healthy polyunsaturated omega-3 fatty acids eicosapentaenoic acid (EPA) and docosahexaenoic acid (DHA), as compared to alpha-linolenic acid (ALA) which needs to be converted by the body to EPA and DHA to be useful. EPA and DHA derived from fish oils have been shown to play an important structural role and influence fluidity in cell membranes. Topically applied plant derived fatty acids, in contrast, are less usable by the skin. However, marine derived fatty acids tend to be unstable and oxidize quickly resulting in bad smell. Thus, there is a need for compositions which increase the stability of marine derived fatty acids. The present invention satisfies this need.

SUMMARY

Oils derived from marine sources, such as fish oils, are particularly high in the polyunsaturated omega-3 fatty acids eicosapentaenoic acid (EPA) and docosahexaenoic acid (DHA), which are helpful for treating various skin conditions and wounds. However, marine oils are more difficult to stabilize than oils from other sources, such as plant oils. The stabilized formulations described herein, comprising tocopherol (Vitamin E), ascorbic acid (Vitamin C), herb extract, and a fat-soluble antioxidant, inhibit degradation and oxidation of omega-3 polyunsaturated fatty acids from marine oils. This invention also relates to methods of making and using the stabilized formulations.

BRIEF DESCRIPTION OF THE DRAWINGS

FIG. 2 shows the fatty acid compositions for the peaks in the chromatograph shown in FIG. 1; EPA (peak #20) and DHA (peak #24) are volume based 19.6% and 12.6%, respectively.

DESCRIPTION

Figure 1:
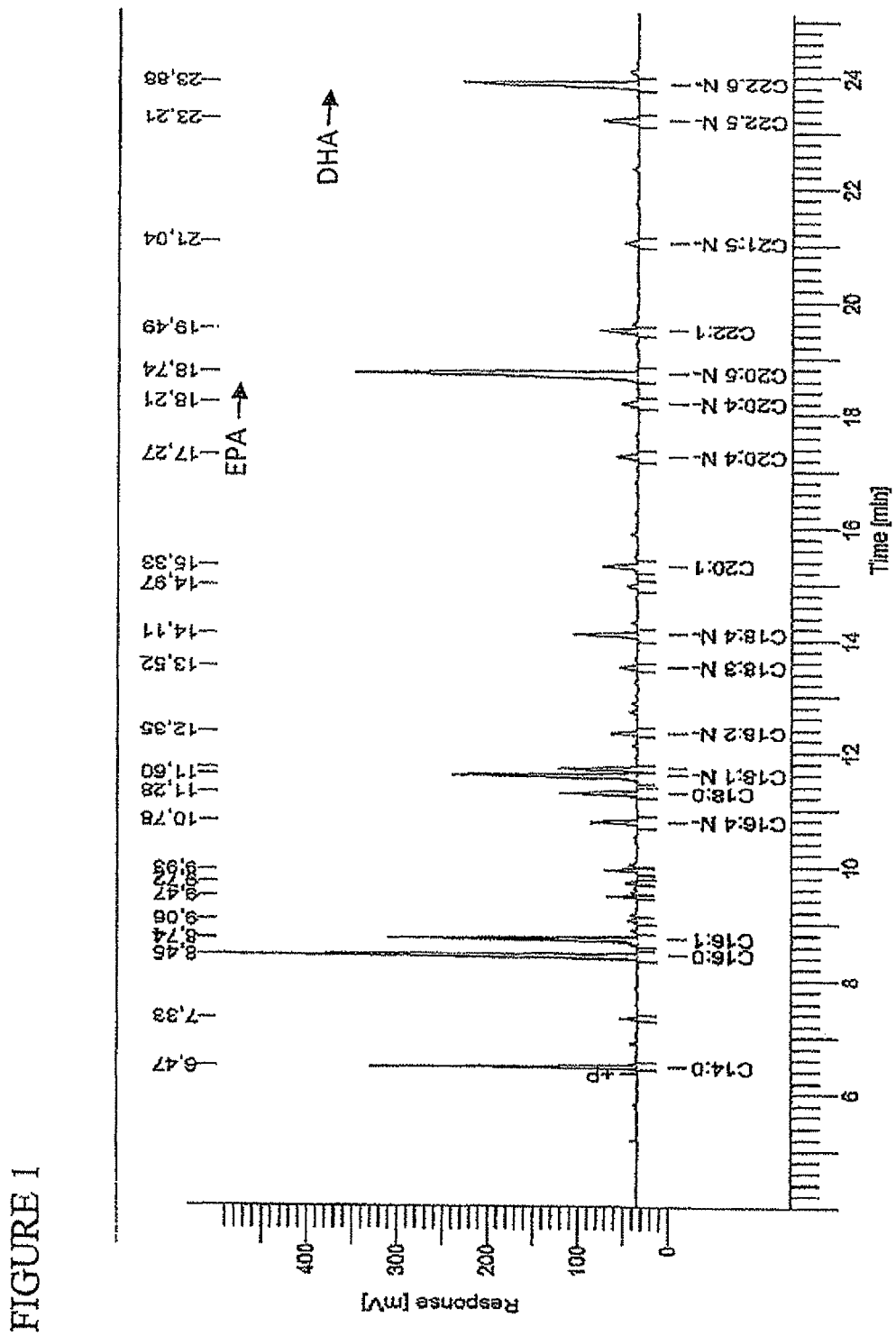
FIG. 1 shows a chromatograph of a marine based oil that can be used in the compositions and methods of the present application.

Marine derived omega-3 polyunsaturated fatty acids are very difficult to stabilize, and are easily oxidized and damaged. They are therefore difficult to use in cosmetics or pharmaceuticals that should have a shelf life of more than 6 months. Commercial fish oils, for example, are usually processed with the addition of natural antioxidants, such as tocopherols. The present inventors have unexpectedly found that the formulation described herein is useful for further inhibiting the oxidation of polyunsaturated oils beyond what is provided by the antioxidants that are added at the time the oil is initially processed. Oxidation studies were conducted and it was found that the present compositions provide additional unexpectedly significant protection of polyunsaturated oils from degradation and/or oxidation.

Described herein is a formulation for stabilizing omega-3 polyunsaturated fatty acids, comprising omega-3 polyunsaturated fatty acids in combination with tocopherol (Vitamin E), ascorbic acid (Vitamin C), herb extract, and a fat-soluble antioxidant. This stabilized formulation can slow the oxidation process down to an acceptable level for use in cosmetic and pharmaceutical creams. In some embodiments, oxidation of the omega-3 polyunsaturated fatty acids is slowed for at least 12 months, such as for at least 24, 23, 22, 21, 20, 19, 18, 17, 16, 15, 14, or 13 months. Oxidation tests are known in the art. Stability of the omega-3 polyunsaturated fatty acids can be evaluated by, for example, odor or smell tests, or more quantitatively by peroxide tests with titration.

Suitable tocopherols include alpha-, beta-, delta-, and gamma-tocopherol and alpha-, beta-, delta- and gammatocotrienol. In certain embodiments, the tocopherol is alpha-tocopherol. The tocopherols can be used in the stabilized formulation in an amount of from about 0.005 to about 0.5% by weight of the total composition, such as about 0.01, 0.02, 0.03, 0.04, 0.05, 0.06, 0.07, 0.08, 0.09, 0.1, 0.2, 0.3, or 0.4% by weight of the composition.

Suitable herb extracts include extracts of rosemary, oregano, basil, marjoram, thyme (timian), black pepper, caraway, cardamom, chives, calorifico, coriander, cumin, dill, garlic, ginger, laurel, nutmeg, onion, parsley, sage, savory and tarragon. In certain embodiments the herb extract is an extract of rosemary. Rosemary (*Rosmarinus Officinalis*) is an aromatic herb and known stabilization additive (see, e.g., Mariutti et al. (2008) *Free Radical Scavenging Activity of Ethanolic Extracts from Herbs and Spices Commercialized in Brazil*, Brazilian Archives of Biology and Technology 53:1225-1232 and Wojdylo et al. (2007) *Antioxidant Activity and Phenolic Compounds in 32 Selected Herbs*, Food chemistry 105:940-949).

"Herb extract" is a generic term describing a number of different chemical compositions that may contain several different active components. Among the common components that are found in, e.g., rosemary extract are carnosol, carnosic acid, methoxy carnosic acid, rosmarinic acid, rosmanol and rosmaridiphenol, in different proportions depending on the individual extract. Rosemary extract may also contain quinine and several additional beneficial substances with antioxidant properties, like eucalyptol, borneol, pinene, and camphor.

The herb extract can be, for example, an alcohol or aqueous abstract, and methods of making herb extracts are known in the art. In addition, numerous herb extracts are available commercially. Examples include Rosemary Leaf Extract available from MakingCosmetics Inc. (Renton, Wash., USA) and GUARDIAN™ Rosemary Extract available from Earth Supplied Products LLC (Naples, Fla.). The Rosemary Leaf Extract from MakingCosmetics Inc., used in the examples described below, is extracted in glycerin and water.

The term "rosemary extract" as used herein encompasses not only a rosemary extract per se, but also a composition to which the individual active components, such as are noted above, are added to the composition individually, or in individual combinations, from synthetic or natural sources, either from rosemary or from starting material other than rosemary, in amounts equivalent to those found in the rosemary extract.

The herb extract can be used in the stabilized formulation in an amount of from about 0.05 to about 5% by weight of the total composition, such about 0.1, 0.2, 0.3, 0.4, 0.5, 0.6, 0.7, 0.8, 0.9, 1, 2, 3, or 4% by weight of the composition.

Suitable fat-soluble antioxidants are available on the market and include synthetic antioxidants such as BHT (butylated hydroxytoluene), BHA (butylated hydroxyanisole) and TBHQ (tertiary butyl hydroquinone). BHT, for example, is a widely used food preservative that neutralizes free radicals and prevents auto-oxidation of organic material. The fat-soluble antioxidant can be used in the stabilized formulation in an amount of from about 0.01 to about 10% by weight of the total composition, such as about 0.02, 0.03, 0.04, 0.05, 0.1, 0.2, 0.25, 0.3, 0.4, 0.5, 1, 2, 3, 4, 5, 6, 7, 8, or 9% by weight of the composition.

The omega-3 polyunsaturated fatty acids can be derived from one or more oil sources including marine oils (e.g. fish, krill, marine algae, and calamari oils), seed oils, plant oils, and algal oils, comprising at least one fatty acid selected from the group consisting of DHA and EPA. The term "fatty acid" as used herein refers to a fatty acid that may be in free form, a monoglyceride, a diglyceride, a triglyceride, an ester or solvate thereof, a pharmaceutically acceptable salt thereof, or combinations thereof. The omega-3 polyunsaturated fatty acids are generally provided in a marine oil, for example a fish oil. Fish oils, particularly fish oils from cold water oily fish, are particularly rich in DHA and EPA. Examples of fish high in omega-3 oil include salmon, pilchards, tuna, herring, cod, anchovies, sardines, mackerel, sable fish, smelts, whitefish, hoki fish, and some varieties of trout. In certain embodiments the omega-3 polyunsaturated fatty acids are from oil which is pharmaceutically acceptable according to Pharmacopeia standards (i.e. pharmaceutical grade oils). Such oils include commercially-available marine omega oils such as Omega-3 Fish Oil (Lysi Ltd., Iceland). Omega-3 Fish Oil from Lysi Ltd. was used in the examples described below. Marine oils can be used in the stabilized formulation in an amount of from about 0.001-99% by weight of the total composition, such as from about 0.01-99, 0.1-99, 1-99, 10-99, 20-99, 30-99, 40-99, 50-99, 60-99, 70-99, or 80-99% by weight of the composition.

In certain embodiments, the marine oil itself comprises from about 0.1-60% by weight of the marine oil, such as from about 5-60, 10-40, or 10-20% by weight of DHA and/or EPA from about 0.1-60, such as from about 5-60, 10-40, or 10-20% by weight of EPA. The marine oil can also comprise other fatty acid or non-fatty acid components naturally found in fish or added to commercial marine oils.

Tests and trials have shown that formulations having as little as 0.15% (w/w) of EPA and DHA have substantial affects on the process of healing damaged skin (data not shown).

In certain embodiments, the omega-3 polyunsaturated fatty acids can be from particulates of the scaffold material prepared in accordance with Sigurjonsson et al., U.S. patent application Ser. No. 12/899,123, filed on Oct. 6, 2010, rather than from fish oil. The particulates are prepared by grinding the scaffold material to a grain size of about 0.01 to about 5 mm in diameter, such as about 0.02, 0.03, 0.04, 0.05, 0.06, 0.07, 0.08, 0.09, 0.1, 0.2, 0.3, 0.5, 0.6, 0.7, 0.8, 0.9, 1, 2, 3, or 4 mm in diameter. Alternatively, the scaffold material described in U.S. patent application Ser. No. 12/899,123 can be dissolved (e.g. partially or completely gelatinized in an acidic or basic solution) rather than particulated.

The stabilized formulations described above, comprising omega-3 polyunsaturated fatty acids, tocopherol (Vitamin E), ascorbic acid (Vitamin C), herb extract, and a fat-soluble antioxidant, are useful for treating various dermatological conditions, including dry skin, atopic dermatitis, allergic contact dermatitis, and radiation dermatitis. The formulations may also be useful for treating first and second degree wounds, sunburns, superficial injuries, abrasions, cuts, surgical wounds, pressure ulcers, venous stasis ulcers, ulcers caused by mixed etiologies, diabetic ulcers, donor sites, and grafts. The stabilized formulations are suitable for treating any type of dry skin where callosity formation is a problem. The diabetic foot, for example, is particularly susceptible to the loss of intercellular lipids in the skin.

The stabilized formulations can also be used in compositions comprising the stabilized formulations in combination with one or more additional therapeutically active compounds (i.e. active agents), such as exfoliates or other agents that may increase the permeability of the skin so that the polyunsaturated fatty acids can enter the skin more easily (e.g. alpha hydroxyl acids (AHAs) such as glycolic acid lactic acid), water retaining chemicals and moisturizers (e.g. urea, propylene glycol (PPG)), and polyacrylic acid. Other suitable additional therapeutically active compounds include antiseptics, antimicrobial agents, antivirals, antifungals, antiparasitics, anti-inflammatory agents, antioxidants, drugs, proteins, and peptides.

In certain embodiments the compositions comprise (in addition to the stabilized formulation) one or more AHAs. AHAs may improve the penetration of the polyunsaturated fatty acids into the skin; improve the penetration of other ingredients of the compositions (e.g. urea) into the skin; and work in concert with the components of the stabilized formulation to enhance the stability of the polyunsaturated fatty acids.

In certain embodiments the compositions comprise AHA and urea, and can further comprise one or more of polypropylene glycol, an aqueous carrier, paraffin liquid, petrolatum, lanolin alcohol, cetearyl alcohol, and fragrance.

In addition, one or more pharmaceutically and/or cosmetically acceptable diluents, excipients or carriers can be added. For example, the composition may comprise substances which assist in its application or storage stability, such as, e.g., stabilizers, preservatives, pharmaceutical adjuvants, water, buffer substances, thickening agents, emulsifiers, and the like. The techniques of preparing pharmaceutical compositions are generally well known in the art as exemplified by *Remington's Pharmaceutical Sciences,* 16th Ed. Mack Publishing Company, 1980. Moreover, for human administration, preparations may need to meet sterility, pyrogenicity, and general safety and purity standards, e.g. as required by the FDA Office of Biological Standards.

In certain embodiments, the compositions are topically administered. "Topical" administration means local, external administration to skin and/or to a wound. The composition may be topically administered directly to all or to part of the area of skin or the wound in need of treatment, or peripherally to the skin area or the wound.

For topical administration, for example, the compositions can be formulated as a gel, ointment, cream, balm, or lotion. Topical administration can also be accomplished with a liquid spray, an aerosol, or via iontophoresis, or through the use of liposomes, microbubbles and/or microcapsules. Gels, ointments and creams may be formulated, for example, with an aqueous or oily base with the addition of suitable thickening (e.g., wax, beeswax, PEG 4000, PEG 600, hard paraffin) and/or gelling agents (e.g., hydroxypropyl cellulose). Lotions may be formulated with an aqueous or oily base and can also generally contain one or more emulsifying agents (e.g., wool wax alcohol, fatty acid glycol esters), stabilizing agents (e.g., polyoxyethylene sorbitan monolaurate, carboxy methyl cellulose), dispersing agents (e.g., sodium oleate, propylene glycol), suspending agents (e.g., methyl cellulose, chitosan, accacia, carboxymethyl cellulose, tragacanth, pectin), thickening agents, and/or coloring agents (e.g., dyes, lackes). Other conventional pharmaceutical excipients for topical application include pluronic gels, polaxamer gels, hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (carbopols). Suitable carriers also include creams/ointments conventionally used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA. In certain embodiments, the present composition comprises wax in an amount ranging from 1-50% by weight based on 100% by weight of the total composition, such as 5-40%, 10-30%, 15-25%, or 20% by weight based on 100% by weight of the total composition.

The stabilized formulation can be applied directly to the skin or wound as a gel, ointment, liquid, cream, or the like as described above. Alternatively, the stabilized formulation is administered in the form of a wound dressing. As used herein, the terms "wound dressing" and "dressing" refer broadly to any substrate when prepared for, and applied to, a wound for protection, absorbance, drainage, improvement of cell environment, etc., and may include any one of the numerous types of substrates and/or backings that are commercially available, including films (e.g., polyurethane films), hydrocolloids (e.g., hydrophilic colloidal particles bound to polyurethane foam), hydrogels (e.g., cross-linked polymers containing about at least 60% water), foams (hydrophilic or hydrophobic), calcium alginates (e.g. non-woven composites of fibers from calcium alginate), silicone, collagen, keratin, and cellophane (e.g. cellulose with a plasticizer). The substrate can also be a fish skin extracellular matrix (ECM) material (i.e. scaffold material) as described in Sigurjonsson et al., U.S. patent application Ser. No. 12/899,123, filed on Oct. 6, 2010, or a polyurethane wound dressing such as the wound dressing described in Sigurjonsson, U.S. Pat. No. 7,230,154.

For example, the stabilized formulation can be applied to the surface of, or incorporated into, a solid contacting layer such as a dressing gauze or matrix. Suitable gauze dressings may include, for example, dry woven or non-woven sponges, swabs, bandages and wraps with varying degrees of absorbency. Exemplary fabric composition may include, for example, cotton, polyester or rayon. In certain embodiments, gauzes and non-woven dressings may be available sterile or non-sterile in bulk and with or without an adhesive border. In certain embodiments the dressings also comprise one or more additional pharmaceutically active compound and/or carrier agent, including for example, saline, oil, zinc salts, petrolatum, xeroform and scarlet red.

An example composition suitable for application to a wound, including an open wound, is a sterile liquid composition comprising the stabilized formulation in combination with polyacrylic acid, polyacrylic acrylate, xanthan gum, guar gum, hydoxyl cellulose, and/or silicon.

In another embodiment, the omega-3 polyunsaturated fatty acids described herein are combined with AHA in the absence of at least one of the other components of the stabilized formulation (i.e. tocopherol (Vitamin E), ascorbic acid (Vitamin C), herb extract, and a fat-soluble antioxidant). In this embodiment, the composition can comprise any one or more of the additional therapeutically active compounds and pharmaceutically and/or cosmetically acceptable diluents, excipients or carriers described herein. A composition that does not comprise the stabilized formulation can be formulated for topical application as described herein and sealed in an air tight container suitable for a single use. Such a composition can be used to treat any of the skin conditions and/or wounds described herein, for example a skin condition and/or wound present on the diabetic foot.

The dosage regimen for treating skin conditions and/or wounds is selected in accordance with a variety of factors, including the age, weight, sex, and medical condition of the patient, the severity of the condition, the route of administration, pharmacological considerations such as the activity, efficacy, pharmacokinetic and toxicology profiles of the particular composition used, whether a dressing or drug delivery system is used and whether the composition is administered as part of a drug combination.

The doses may be administered in single or divided applications. The doses may be administered once, or application may be repeated. Application may be repeated weekly until skin and/or wound healing is promoted, or a repeat application may be made in the event that healing slows or is stalled. Doses may be applied 1-7 days apart, or more. In the case of a chronic skin condition or wound, repeat applications may be made, for example, one or more times per day, weekly, or bi-weekly, or monthly or in any other frequency for example if and when healing slows or is stalled. For some indications more frequent dosing such as hourly application may be employed.

"Treatment" or "treating," as used herein, refers to complete elimination as well as to any clinically or quantitatively measurable healing or alleviation of the symptoms of the skin condition and/or wound. A "therapeutically effective amount" means the amount of a composition that, when administered to a subject for treating a skin condition and/or wound, is sufficient to effect a desirable treatment for the skin condition and/or wound. The "therapeutically effective amount" will vary depending on the particular composition, the condition and its type and severity, and the age, weight, etc., of the subject to be treated. A "therapeutically effective amount" need not result in a complete cure, but may provide partial relief of one or more symptoms or retard the progression of a condition such as dryness.

"Patient" or "subject" refers to animals, and can include any mammal, such as humans, rats, mice, cats, dogs, goats, sheep, horses, monkeys, apes, rabbits, cattle, etc. The mammalian subject can be in any stage of development including adults, children, infants, and neonates.

As used herein, the singular forms "a", "an" and "the" include plural referents unless the context clearly dictates otherwise.

The publications disclosed herein are provided solely for their disclosure prior to the filing date of the present application. Nothing herein should be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference in their entirety.

While the disclosure has been described in detail with reference to certain embodiments thereof, it will be apparent to one skilled in the art that various changes can be made, and equivalents employed, without departing from the scope of the disclosure. In addition, the following examples are illustrative only and should not be considered as limiting the disclosure in any way.

EXAMPLES

Example 1

Stabilized Formulations (wt %)

1) 0.05% Vit.E
   3% Vit.C
   0.5% Rosemary
   0.25% BHT or BHA
   96.2% Omega-3 Fish Oil (Lysi Ltd., Iceland)
2) 0.25% Vit.E
   2% Vit.C
   0.25% Rosemary
   0.25% BHT or BHA
   97.25% Omega-3 Fish Oil (Lysi Ltd., Iceland)
3) 0.1% Vit.E
   1% Vit.C
   0.5% Rosemary
   0.1% BHT or BHA
   98.3% Omega-3 Fish Oil (Lysi Ltd., Iceland)
4) 0.05% Vit.E
   1% Vit.C.
   0.25% Rosemary
   0.5% BHT or BHA
   98.2% Omega-3 Fish. Oil (Lysi Ltd., Iceland)

Example 2

Foot Cream Formulations and Preparation Protocol

| Formulation I | Amount | Purpose | Part |
|---|---|---|---|
| Lanolin alcohol | 27% | Emollient | A |
| Cetearyl alcohol | | Emulsion stabiliser | |
| Petrolatum | | Emollient | |
| Urea | 10% | Humectant | C |
| AHA | 7% | Peeling agent | B |
| Paraffine liquid | 5% | Emollient | A |
| Polypropylene glycol | 4% | Humectant | B |
| Stabilized formulation | 3% | — | C |
| Sodium acrylates copolymer PPG-1 | 2.5% | Thickener | C |
| Trideceth-6 | | Thickener | |
| Polydecane | | Thickener | |
| Steareth-100 | 1% | Emulsifier | B |
| Steareth-2 sucrose | | Emulsifier | |
| Xanthan Gum | | Thickener | |
| Tocopherol | 1% | anti oxidant | C |
| methyl paraben | 0.1% | Preservative | C |
| ethyl paraben | | Preservative | |
| propyl paraben | | Preservative | |
| Phenoxyethanol | | Preservative | |
| Fragrance oil | 0.01% | fragrance oil* | |
| Aqua | 39.4% | Aqua | B |
| Triethanolamine | if needed | pH modifier | |

*e.g. almond, vanilla, green tea, mountain rain, vetever, pinapple, grapefruit . . .

| Formulation II | Amount | Purpose | Part |
|---|---|---|---|
| Lanolin alcohol | 27% | Emollient | A |
| Cetearyl alcohol | | emulsion stabiliser | |
| Petrolatum | | Emollient | |
| Urea | 10% | Humectant | C |
| AHA | 7% | peeling agent | B |
| Paraffine liquid | 5% | Emollient | A |
| Polypropylene glycol | 4% | Humectant | B |
| Stabilized formulation | 3% | — | C |
| Sodium polyacrylate | 2% | Thickener | C |
| Mineral oil (USA/CTFA) | | Thickener | |
| Trideceth-6 | | Thickener | |
| Steareth-100 | 1% | Emulsifier | B |
| Steareth-2 sucrose | | Emulsifier | |
| Xanthan Gum | | Thickener | |
| Tocopherol | 1% | anti oxidant | C |
| methyl paraben | 0.1% | Preservative | C |
| ethyl paraben | | Preservative | |
| propyl paraben | | Preservative | |
| Phenoxyethanol | | Preservative | |
| Fragrance oil | 0.01% | fragrance oil* | |
| Aqua | 39.9% | Aqua | B |
| Triethanolamine | if needed | pH modifier | |

*e.g. almond, vanilla, green tea, mountain rain, vetever, pinapple, grapefruit . . .

| Formulation III | Amount | Purpose | Part |
|---|---|---|---|
| Lanolin alcohol | 27% | Emollient | A |
| Cetearyl alcohol | | emulsion stabiliser | |
| Petrolatum | | Emollient | |
| Urea | 10% | Humectant | C |
| AHA | 7% | peeling agent | B |
| Paraffine liquid | 5% | Emollient | A |
| Polypropylene glycol | 4% | Humectant | B |
| Stabilized formulation | 3% | — | C |
| Sodium polyacrylate | 2% | Thickener | C |
| Mineral oil (USA/CTFA) | | Thickener | |
| Trideceth-6 | | Thickener | |
| Sucrose Palmitate | 1% | Emulsifier | B |
| Glyceryl Stearate | | Emulsifier | |
| Glyceryl Stearate Citrate | | Emulsifier | |
| Mannan | | Thickener | |
| Xanthan Gum | | Thickener | |
| Tocopherol | 1% | anti oxidant | C |
| methyl paraben | 0.1% | Preservative | C |
| ethyl paraben | | Preservative | |
| propyl paraben | | Preservative | |
| Phenoxyethanol | | Preservative | |
| Fragrance oil | 0.01% | fragrance oil* | |

-continued

| Formulation III | Amount | Purpose | Part |
|---|---|---|---|
| Aqua | 39.9% | Aqua | B |
| Triethanolamine | if needed | pH modifier | |

*e.g. almond, vanilla, green tea, mountain rain, vetever, pinapple, grapefruit . . .

| Formulation IV | Amount | Purpose | Part |
|---|---|---|---|
| Lanolin alcohol | 27% | Emollient | A |
| Cetearyl alcohol | | Emulsion stabiliser | |
| Petrolatum | | Emollient | |
| Urea | 10% | Humectant | C |
| AHA | 7% | Peeling agent | B |
| Paraffine liquid | 5% | Emollient | A |
| Polypropylene glycol | 4% | Humectant | B |
| Stabilized formulation | 3% | — | C |
| Sodium acrylates copolymer PPG-1 | 2.5% | Thickener | C |
| Trideceth-6 | | Thickener | |
| Polydecane | | Thickener | |
| Steareth-100 | 1% | Emulsifier | B |
| Steareth-2 sucrose | | Emulsifier | |
| Xanthan Gum | | Thickener | |
| Tocopherol | 1% | anti oxidant | C |
| methyl paraben | 0.1% | Preservative | C |
| ethyl paraben | | Preservative | |
| propyl paraben | | Preservative | |
| Phenoxyethanol | | Preservative | |
| Rosemary extract | 0.05% | anti oxidant | C |
| Fragrance oil | 0.01% | fragrance oil* | |
| Aqua | 38.9% | Aqua | B |
| Triethanolamine | if needed | pH modifier | |

*e.g. almond, vanilla, green tea, mountain rain, vetever, pinapple, grapefruit . . .

Preparation
1. Heat phases A and B separately up to T=70-80° C., preferrably in a water bath.
2. Phase B is put in a mixer ans phase A poured gently into the mixture with continous powerful stirring.
3. Continue stirring while mixture cools down to 40° C.
4. Add phase C to the mixture.
5. Continue with powerful stirring until mixture has cooled down to room temperature
6. Add fragrance oil
7. Measure pH and adjust with trethanolamine if necessary (preferred pH=3.0-3.5)

The first step in preparation of the cream is to make two different solutions; a fat based solution and an aqueous solution. The fat based solution is prepared by heating the oils and fat-soluble chemicals (lanolin alcohol, ceteryl alcohol, petrolatum, paraffin liquid . . . ) up 70-80° C. The aqueous solution is prepared by heating the water and water-soluble chemicals (aqua, polypropylene glycol, AHA . . . ) up to the same temperature as the fat-based solution. When both mixtures are heated they are carefully mixed together by pouring them into a powerful stirrer. The oils are first put into the mixer and then the aqueous solution is poured in little by little. The mixture should be stirred the whole time while cooling down, or it will separate. When cooled down to about 40° C., the polyunsaturated fatty acids (i.e. the stabilized formulation) and urea are mixed together with thickening agents, antioxidants and preservatives and added to the mixture. The cream is now kept in the mixer with continuously stirred until cooled down to room temperature. Finally fragrance is added to the cream and the pH is measured and adjusted to pH of 2-5 (such as 3.0-3.5) if necessary with triethanolamin.

The proportion of the active ingredients (polyunsaturated fatty acids, AHA and urea) can vary at least about ±2% without the cream losing its quality. A small variation in concentration is also acceptable for the carriers (e.g. the various thickening and emulsifying agents).

Example 3

Skin Cream Formulations

A. Stabilized formulation, purified water, liquid paraffin (mineral oil), petrolatum, alcohol, glyceryl stearate, PEG-100 stearate, paraffin, lecithin, polysorbate 60, DEA-cetyl phosphate, dimethicone, carbomer, imidazolidinyl urea, methylparaben, propylparaben, triethanolamine, fragrance.

B. Stabilized formulation, purified water, olive oil, glycerin, pentylene glycol, palm glycerides, vegetable oil, hydrogenated lecithin, squalene, betaine, palmitamide MEA, sarcosine, acetamide MEA, hydroxethyl cellulose, sodium carbomer, xanthan gum.

C. Stabilized formulation, purified water, liquid paraffin, ethylene glycol monostearate, stearic acid, propylene glycol, paraffin wax, squalene, avocado oil, trolamine/sodium alginate, triethanolamine, cetyl palmitate, methylparaben (sodium salt), sorbic acid (potassium salt), polyparaben (sodium salt), fragrance.

Example 4

Wound Guard Formulations

A. Stabilized formulation, alpha hydroxyl acid (AHA), purified water, liquid paraffin (mineral oil), petrolatum, alcohol, glyceryl stearate, PEG-100 stearate, paraffin, lecithin, polysorbate 60, DEA-cetyl phosphate, dimethicone, carbomer, imidazollidinyl urea, methylparaben, propylparaben, triethanolamine, fragrance.

B. Stabilized formulation, alpha hydroxyl acid (AHA), purified water, liquid paraffin, ehtylene glycol monosterate, stearic acid, propylene glycol, paraffin wax, squalene, avocado oil, trolamine/sodium alginate, triethanolamine, cetyl palmitate, methylparaben (sodium salt), sorbic acid (potassium salt), polyparaben (sodium salt), fragrance.

C. Stabilized formulation, alpha hydroxyl acid (AHA), purified water, olive oil, glycerin, pentylene glycol, palm glycerides, vegetable oil, hydrogenated lecithin, squalene, betaine, palmitamide MEA, sarcosine, acetamide MEA, hydroxyethyl cellulose, sodium carbomer, xanthan gum.

Example 5

Hydrocolloid Wound Dressing

Stabilized Formulation:
0.05% Vit.E
3% Vit.C
0.5% Rosemary extract
0.25% BHT or BHA
96.2% Omega-3 Fish Oil (Lysi Ltd., Iceland)

The Omega3 component (stabilized formulation) is added to a hydrocolloid component that has been heated to become viscous. The components are then mixed together, and the omega3-hydrocolloid mixture is poured onto molds and left for cooling.

Example 6

Wound Contact Layer

Stabilized Formulation:
0.1% Vit.E

1% Vit.C
0.5% Rosemary extract
0.1% BHT or BHA
98.3% Omega-3 Fish Oil (Lysi Ltd., Iceland)

The Omega3 component (stabilized formulation) is mixed together with a hydrogel component. The omega3-hydrogel mixture is then applied to a polyurethan dressing as a wound contact layer (i.e. applied to the side of the polyurethan wound dressing that will be proximal to the wound bed).

Example 7

Omega3 Collagen Wound Dressing

Stabilized Formlation:
0.05% Vit.E
3% Vit.C
0.5% Rosemary extract
0.25% BHT or BHA
96.2% Omega-3 Fish Oil (Lysi Ltd., Iceland)
Wound Dressing Component:

A fish skin ECM (scaffold material) is created as described in Sigurjonsson et al., U.S. patent application Ser. No. 12/899,123, filed on Oct. 6, 2010. The scaffold material is hydrolized until the texture becomes like web paper. The stabilized formulation is poured into the material and material kneaded.

Example 8

Omega3 Collagen Wound Dressing

A fish skin ECM (scaffold material) is created as described in Sigurjonsson et al., U.S. patent application Ser. No. 12/899,123, filed on Oct. 6, 2010. The scaffold material is hydrolized until the texture becomes like web paper. Omega-3 Fish Oil (Lysi Ltd., Iceland) is poured into the material so that the w/w of the components becomes 3/97 and the material is kneaded to mix the fish oil into the scaffold material.

Example 9

Omega3 Keratin Wound Dressing

Stabilized Formulation:
0.1% Vit.E
1% Vit.C
0.5% Rosemary extract
0.1% BHT or BHA
98.3% Omega-3 Fish Oil (Lysi Ltd., Iceland)

A keratin matrix is created as described in Kelly et al., U.S. Patent Application Publication No. 2009/0105456 A1. The Omega3 component (stabilized formulation) is added to the keratin composition before the casting step of the keratin manufacturing process in the ratios 1/99 w/w.

The invention claimed is:

1. A composition comprising:
   (i) a stabilized formulation comprising:
      0.05% to 0.25% tocopherol;
      1% to 3% vitamin C;
      0.25% to 0.5% of an herb extract;
      0.1% to 0.5 of a fat-soluble antioxidant selected from the group consisting of BHT (butylated hydroxytoluene), BHA (butylated hydroxyanisole), TBHQ (tertiary butyl hydroquinone), and combinations thereof; and
      a balance of fish oil, wherein the fish oil comprises omega-3 polyunsaturated fatty acids; and
   (ii) one or more emollients, humectants, or any combination thereof, wherein the composition includes 1% to 5% of the stabilized formulation and is formulated for topical administration.

2. The composition of claim 1, wherein the omega-3 polyunsaturated fatty acids comprise one or more of eicosapentaenoic acid (EPA) and docosahexaenoic acid (DHA).

3. The composition of claim 1, wherein the herb extract is selected from the group consisting of rosemary, oregano, basil, marjoram, thyme, black pepper, caraway, cardamom, chives, colorifico, coriander, cumin, dill, garlic, ginger, laurel, nutmeg, onion, parsley, sage, savory and tarragon extracts, and combinations thereof.

4. The composition of claim 3, wherein the herb extract is a rosemary extract.

5. The composition of claim 1, wherein the fat-soluble antioxidant is BHT.

6. The composition of claim 1, wherein the composition further comprises one or more additional active agents and/or one or more pharmaceutically acceptable diluents, excipients and carriers.

7. The composition of claim 6, wherein the composition comprises one or more exfoliates, moisturizers, antiseptics, antimicrobial agents, antivirals, antifungals, antiparasitics, anti-inflammatory agents, antioxidants, drugs, proteins, peptides, or combinations thereof.

8. The composition of claim 6, wherein the composition comprises alpha hydroxy acid (AHA).

9. The composition of claim 8, wherein the composition comprises AHA and urea.

10. The composition of claim 6, wherein the composition comprises polyacrylic acid.

11. The composition of claim 8, wherein the AHA is one of glycolic acid or lactic acid.

12. The composition of claim 11, wherein glycolic acid is added to the composition in amount ranging from about 5% to 9%.

13. A wound dressing comprising:
   I. a stabilized formulation comprising:
      0.05% to 0.25% tocopherol;
      1% to 3% vitamin C;
      0.25% to 0.5% herb extract;
      0.1% to 0.5 of a fat-soluble antioxidant selected from the group consisting of BHT (butylated hydroxytoluene), BHA (butylated hydroxyanisole), TBHQ (tertiary butyl hydroquinone), and combinations thereof; and
      a balance of fish oil, wherein the fish oil comprises omega-3 polyunsaturated fatty acids; and
   II. a solid or semi-solid substrate, wherein the stabilized formulation is added to the solid or semi-solid substrate to form the wound dressing prepared for application to a wound for protection, absorbance, drainage, or improvement of cell environment.

14. The wound dressing of claim 13, wherein the solid or semi-solid substrate includes at least one of a film, a hydrocolloid, a hydrogel, a foam, an alginate, a silicone, collagen, keratin, cellophane, a fish skin extracellular matrix (ECM), or a polyurethane wound dressing.

15. A method for treating a skin condition and/or wound, comprising applying the composition of claim 1 to the skin condition and/or wound.

16. The method of claim 15, wherein the skin condition and/or wound is selected from the group consisting of dry skin, atopic dermatitis, allergic contact dermatitis, radiation dermatitis, first and second degree wounds, sunburns, superficial injuries, abrasions, cuts, surgical wounds, pressure ulcers, venous stasis ulcers, ulcers caused by mixed etiologies, diabetic ulcers, donor sites, and grafts.

17. The method of claim 16, wherein the skin condition and/or wound is a diabetic ulcer.

18. The method of claim 17, wherein the diabetic ulcer is a foot ulcer.

\* \* \* \* \*